United States Patent
Qvit-Raz

(10) Patent No.: US 10,064,797 B2
(45) Date of Patent: Sep. 4, 2018

(54) TOPICAL FORMULATIONS FOR UV PROTECTION

(71) Applicant: TOPGENIX, INC., Menlo Park, CA (US)

(72) Inventor: Noga Qvit-Raz, Menlo Park, CA (US)

(73) Assignee: TOPGENIX, INC., Menlo Park, CA (US)

(*) Notice: Subject to any disclaimer, the term of this patent is extended or adjusted under 35 U.S.C. 154(b) by 0 days.

(21) Appl. No.: 15/317,131

(22) PCT Filed: Jun. 15, 2015

(86) PCT No.: PCT/US2015/035803
§ 371 (c)(1),
(2) Date: Dec. 8, 2016

(87) PCT Pub. No.: WO2015/195546
PCT Pub. Date: Dec. 23, 2015

(65) Prior Publication Data
US 2017/0119641 A1 May 4, 2017

Related U.S. Application Data

(60) Provisional application No. 62/013,276, filed on Jun. 17, 2014.

(51) Int. Cl.
*A61K 8/44* (2006.01)
*A61K 8/41* (2006.01)
(Continued)

(52) U.S. Cl.
CPC .............. *A61K 8/44* (2013.01); *A61K 8/41* (2013.01); *A61Q 17/04* (2013.01); *C07C 251/20* (2013.01)

(58) Field of Classification Search
CPC ......... A61K 8/44; A61Q 17/04; C07C 251/20
See application file for complete search history.

(56) References Cited

U.S. PATENT DOCUMENTS

| | | |
|---|---|---|
| 4,259,444 A | 3/1981 | Chakrabarty |
| 5,207,998 A | 5/1993 | Robinson et al. |

(Continued)

FOREIGN PATENT DOCUMENTS

| | | |
|---|---|---|
| EP | 1473028 A1 | 11/2004 |
| EP | 0975227 B1 | 11/2005 |

(Continued)

OTHER PUBLICATIONS

Aethic; Aethic, King's college london to develop first sunscreen based on mycosporine-like amino acids; 1 page; retrieved from the Internet http://www.news-medical.net/news/20120912/Aethic-Kings-College-London-to-develop-first-sunscreen-based-on-mycosporine-like-amino-acids.aspx; Published Sep. 12, 2012.

(Continued)

*Primary Examiner* — Rachael E Bredefeld
(74) *Attorney, Agent, or Firm* — Shay Glenn LLP

(57) ABSTRACT

Novel compounds having a two-armed cyclic structure are described. These novel compounds absorb both ultraviolet (UV)-A and UV-B radiation and are formulated with pharmaceutically acceptable excipients to generate a topical composition which is photoprotective when applied to the skin of a subject. Methods for measuring the photoprotective properties of the novel compounds are described as are methods of protecting against sunburn or sun damage through the application of the topical compositions formulated as described.

13 Claims, 4 Drawing Sheets

(51) Int. Cl.
*A61Q 17/04* (2006.01)
*C07C 251/20* (2006.01)

(56) References Cited

U.S. PATENT DOCUMENTS

| | | | |
|---|---|---|---|
| 5,576,354 | A | 11/1996 | DeFlandre et al. |
| 5,587,150 | A | 12/1996 | Deflandre et al. |
| 5,620,682 | A | 4/1997 | Fogel |
| 6,221,648 | B1 | 4/2001 | Le Page et al. |
| 6,605,286 | B2 | 8/2003 | Steidler et al. |
| 6,787,147 | B1 | 9/2004 | Huner et al. |
| 6,899,866 | B2 | 5/2005 | Bonda |
| 6,926,887 | B2 | 8/2005 | Bonda et al. |
| 7,081,442 | B2 | 7/2006 | Seiberg et al. |
| 8,431,112 | B2 | 4/2013 | Bonda et al. |
| 9,234,204 | B2 | 1/2016 | Qvit-Raz et al. |
| 9,453,232 | B2 | 9/2016 | Qvit-Raz et al. |
| 2009/0130073 | A1 | 5/2009 | Reindl et al. |
| 2009/0232751 | A1 | 9/2009 | Lott et al. |
| 2012/0263661 | A1 | 10/2012 | Grune |
| 2012/0301452 | A1 | 11/2012 | Gueniche et al. |
| 2012/0308525 | A1 | 12/2012 | Greenberg et al. |
| 2014/0044677 | A1 | 2/2014 | Qvit-Raz et al. |

FOREIGN PATENT DOCUMENTS

| | | |
|---|---|---|
| EP | 1789529 A2 | 2/2006 |
| EP | 1322318 B1 | 12/2010 |
| EP | 2561853 A1 | 2/2013 |
| EP | 2364712 B1 | 3/2013 |
| FR | 2803201 A | 7/2001 |
| WO | WO86/02350 A1 | 4/1986 |
| WO | WO89/001970 A2 | 3/1989 |
| WO | WO96/011277 A1 | 4/1996 |
| WO | WO02/039974 A1 | 5/2002 |
| WO | WO2003/020236 A2 | 3/2003 |
| WO | WO2006/013441 A2 | 2/2006 |
| WO | WO2007/039086 A1 | 4/2007 |
| WO | WO2011/150127 A2 | 12/2011 |
| WO | WO2011/151426 A2 | 12/2011 |
| WO | WO2012/150269 A1 | 11/2012 |
| WO | WO2013/044059 A2 | 3/2013 |
| WO | WO2013/181741 A1 | 12/2013 |

OTHER PUBLICATIONS

Balskus et al.; The genetic and molecular basis for sunscreen biosynthesis in cyanobacteria; Science; 329(5999); pp. 1653-1656; Sep. 24, 2010 (with Supporting Online Material).

Boyle; Bacteria could be engineered to produce natural bio-sunscreen; 5 pages; retrieved from the internet http://www.popsci.com/science/article/2010-09/algaes-natural-biosunscreen-could-lead-better-skin-protection; Sep. 9, 2010.

Choffnes et al.; Microbial ecology in states of health and disease; Workshop Summary; National Academies Press; Washington (DC); 89 pages; Dec. 29, 2015; retrieved from the internet (http://www.ncbi.nlm.nih.gov/books/NBK189987/?report+printable).

Costello et al.; Bacterial community variation in human body habitats across space and time; Science; 326(5960); pp. 1694-1697; (Author Manuscript); Dec. 18, 2009.

Davison; Risk mitigation of genetically modified bacteria and plants designed for bioremediation; J. Ind. Microbiol. Biotechnol.; 32(11-12); pp. 639-650; Dec. 2005.

De La Coba et al.; Prevention of the ultraviolet effects on clinical and histopathological changes, as well as the heat shock protein-70 expression in mouse skin by topical application of algal uv-absorbing compounds; Journal of Dematological Science; 55(3); pp. 161-169; Sep. 30, 2009.

Ebanks et al.; Mechanisms regulating skin pigmentation: the rise and fall of complexion coloration; Int. J. Mol. Sci.; 10(9); pp. 4066-4087; Sep. 15, 2009.

Eichenbaum et al.; Use of the lactococcal nisA promoter to regulate gene expression in gram-positive bacteria: comparison of induction level and promoter strenght; Appl. Environ. Microbiol.; 64(8); pp. 2763-2769; Aug. 1998.

Elliot et al.; Defining a bacteriophage T4 late promoter: absence of a "-35" region; Cell; 36(1); pp. 211-219; Jan. 1984.

Fuller; Probiotics in human medicine; Gut; 32(4); pp. 439-442; Apr. 1991.

Gao et al.; Microbial ultraviolet sunscreens; Nat. Rev. Microbiol.; 9(11); pp. 791-802; Oct. 2011.

Gaudu et al.; Respiration capacity and consequences in lactococcus lactis; Antonie Van Leeuwenhoek; 82(1-4); pp. 263-269; Aug. 2002.

Gonzalez et al.; Photostability of commercial sunscreens upon sun exposure and irradiation by ultraviolet lamps; BMC Dermatol.; 7:1; 9 pages; Feb. 26, 2007.

Green; Microbial biogeography: from taxonomy to traits; Science; 320(5879); pp. 1039-1043; May 23, 2008.

Grice et al.; Topographical and temporal diversity of the human skin microbiome; Science; 324(5931); pp. 1190-1192; May 29, 2009 (Author Manuscript).

Grice et al.; The skin microbiome; Nat. Rev. Microbiol.; 9(4); pp. 244-253; (Author Manuscript); Apr. 2011.

Gueniche et al.; Bifidobacterium longum lysate, a new ingredient for reactive skin; Exp. Dermatol.; 19(8); pp. e1-e8; Aug. 2010.

Helionori; For a natural bioprotection against UVA, Esocert approved, Patent FR9916785; 4 pages; retrieved Apr. 3, 2009 from the internet http:www.biosiltech.com/sites/default/files/Helionori.pdf.

Hentges; The anaerobic microflora of the human body; Clin.Infect. Dis.; 16(4); pp. S175-S180; Jun. 1993.

Huang et al.; Industrial production of recombinant therapeutics in *Escherichia coli* and its recent advancements; J. Ind. Microbiol. Biotechnol.; 39(3); pp. 383-399; Mar. 2012.

IGEM 2012 Team Minnesota Project: Synthesizing uv-protective compounds in bacteria; 5 pages; retrieved Jul. 24, 2015 from the Internet http://2012.igem.org/Team:Minnesota/Protective/UV_Absorption.

Joo et al.; Therapeutic advantages of medicinal herbs fermented with lactobacillus plantarum, in topical application and its activities on atopic dermatitis; Phytother. Res.; 23(7); pp. 913-919; Jul. 2009.

Kiatpapan et al.; Genetic manipulation system in propionibacterium; J. Biosci. Bioeng.; 93(1); pp. 1-8; Jan. 2002.

Kim et al.; A xylose-inducible bacillus subtilis integration vector and its application; Gene; 181(1-2; pp. 71-76; Nov. 28, 1996.

Kim et al.; Improvement of a nisin-inducible expression vector for use in lactic acid bacteria; Plasmid; 58(3); pp. 275-283; Nov. 2007.

Klann et al.; Estrogen-like effects of ultraviolet screen 3-(4-methylbenzlidene)-camphor (Eusolex 6300) on cell proliferation and gene induction in mammalian and amphibian cells; Environ. Res.; 97(3); pp. 274-281; Mar. 2005.

Kleerebezem et al.; Controlled gene expression systems for lactic acid bacteria: transferable nisin-inducible expression cassettes for lactococcus, leuconostoc, and *Lactobacillus* spp; Appl. Environ. Microbiol.; 63(11); pp. 4581-4584; Nov. 1997.

Knowland et al.; Sunlight-induced mutagenicity of a common sunscreen ingredient; FEBS Lett.; 324(3); pp. 309-313; Jun. 21, 1993.

Kok et al.; Construction of plasmid cloning vectors for lactic streptococci which also replicate in bacillus subtilis and *Escherichia coli*; Appl. Environ. Microbiol.; 48(4); pp. 726-731; Oct. 1984.

Li et al.; Glutathione protects lactococcus lactis against oxidative stress; Appl. Environ. Microbiol.; 69(10); pp. 5739-5745; Oct. 2003.

Llewellyn et al.; Distribution and abundance of MAAs in 33 species of microalgae across 13 classes; Mar. Drugs; 8(4); pp. 1273-1291; Apr. 2010.

Luchansky et al.; Molecular cloning and deoxyribonucleic acid polymorphisms in lactobacillus acidophilus and lactobacillus gasseri; J. Dairy Sci..; 74(10); pp. 3293-3302; Oct. 1991.

Mierau et al.; 10 years of the nisin-controlled gene expression system (NICE) in lactococcus lactis; Appl. Microbiol. Biotechnol.; 68(6); pp. 705-717; Oct. 2005.

(56) References Cited

OTHER PUBLICATIONS

Nguyen et al.; A food-grade system for inducible gene expression in lactobacillus plantarum using an alanine racemase-encoding selection marker; J. Agric. Food Chem.; 59(10); pp. 5617-5624; May 25, 2011.

Nouaille et al.; Heterologous protein production and delivery systems for lactococcus lactis; Genet. Mol. Res.; 2(1); pp. 102-111; Mar. 31, 2003.

Ouwehand et al.; Probiotics for the skin: a new area of potential application; Lett. Appl. Microbiol.; 36(5); pp. 327-331; Apr. 2003.

Packaged Facts; The U.S. market for suncare and lipcare products: market report; © 2015; 7 pages; retrieved Jul. 23, 2015 from the internet: http://www.packagedfacts.com/sitemap/product.asp-?productid=222308.

Padwa; Cyano-o-silyhydroxylamines as nitrone blocking groups. J. Chem. Soc., Chem. Commun.; 10; pp. 789-790; May 1986.

Perez-Arellano et al.; Construction of compatible wide-host-range shuttle vectors for lactic bacteria and *Esherichia coli*; Plasmid; 46(2); pp. 106-116; Sep. 2001.

Pouwels et al.; Genetics of lactobacilli: plasmids and gene expression; Antonie Van Leeuwenhoek; 64(2); pp. 85-107; Jun. 1993.

Rastogi et al.; Photoprotective compounds from marine organisms; J. Ind. Microbiol. Biotechnol.; 37(6); pp. 537-558; Jun. 2010.

Reid et al.; Potential uses of probiotics in clinical practice; Clin. Microbiol. Rev.; 16(4); pp. 658-672; Oct. 2003.

Rodrigues et al.; *Medicago* spp. Extracts as promising ingredients for skin care products; Industrial Crops and Products; 49; pp. 634-644; Aug. 31, 2013.

Rolfe; The role of probiotic cultures in the control of gastrointestinal health; J. Nutr.; 130(2S Suppl); pp. 396S-402S; Feb. 2000.

Rud et al.; A synthetic promoter library for constitutive gene expression in lactobacillus plantarum; Microbiology; 152(Pt 4); pp. 1011-1019; Apr. 2006.

Russo et al.; Learning how to manipulate dna's double helix has fuelled job growth in biotechnology during the past 50 years; 421(6921); pp. 456-457; Jan. 23, 2003.

Sambandan et al.; Sunscreens: an overview and update; J. Am. Acad. Dermatol.; 64(4); pp. 748-758; Apr. 2011.

Sanchez et al.; General and specialized vectors derived from pBM02, a new rolling circle replicating plasmid of lactococcus lactis; Plasmid.; 51(3); pp. 265-271; May 2004.

Shareck et al.; Cloning vectors based on cryptic plasmids isolated from lactic acid bacteria: their characteristics and potential applications in biotechnology; Crit. Rev. Biotechnol.; 24(4); pp. 155-208; Jan. 1, 2004.

Snick et al.; Mycosporine-like amino acids and related gadusols: biosynthesis, accumulation, and uv-protective functions in aquatic organisms; Ann. Rev. Physiol.; 64; pp. 223-262; Mar. 2002.

Sorensen; Towards universal systems for recombinant gene expression; Microbial Cell Factories; 9:27; 4 pages; Apr. 2010.

Steidler et al.; Biological containment of genetically modified lactococcus lactis for intestinal delivery of human interleukin 10; Nat. Biotechnol.; 21(7); pp. 785-789; Jul. 2003.

Steidler et al.; Delivery of therapeutic proteins to the mucosa using genetically modified microflora; Expert Opin. Drug Deliv.; 2(4); pp. 737-746; Jul. 2005.

Steidler et al.; Therapeutic drug delivery by genetically modified lactococcus lactis; Ann. N Y Acad. Sci.; pp. 176-186; Sep. 3, Aug. 2006.

Stern; Clinical practice. Treatment of photoaging; N. Engl. J. Med.; 350(15); pp. 1526-1534; Apr. 2004.

Storm et al.; On in 3 prescriptions are never redeemed: primary nonadherence in an outpatient clinic; J. Am. Acad. Dermatol.; 59(1); pp. 27-33; Jul. 2008.

Tarras-Wahlberg et al.; Changes in ultraviolet absorption of sunscreens after ultraviolet irradiation; J. Invest. Dermatol.; 113(4); pp. 547-553; Oct. 1999.

Telemet Inc.; Make snow; © 2015; 6 pages; Jul. 23, 2015 retrieved from the internet http://www.telemet.com/snow/snomax.asp.

Torres et al. A new uv-b absorbing mycosporine with photo protective activity from the lichenized ascomycete collema cristatum; Eur. J. Biochem.; 271(4); pp. 780-784; Feb. 2004.

Van De Guchte et al.; Heterologous gene expression in *Lactococcus lactis* subsp. *lactis*: synthesis, secretion, and processing of the bacillus subtilis neutral protease; Appl. Environ. Microbiol.; 56(9); pp. 2606-2611; Sep. 1990.

Van Der Vossen et al.; Characterization of transcription initiation and termination signals of the proteinase genes of lactococcus lactis Wg2 and enhancement of proteolysis in L. lactis; Appl. Environ. Microbiol.; 58(9); pp. 3142-3149; Sep. 1992.

Vangelista et al.; Engineering of lactobacillus jensenii to RANTES and a CCR5 antagonist analogue as live HIV-1 blockers; Antimicrob. Agents Chemother.; 54(7); pp. 2994-3001; Jul. 2010.

Wallace et al.; A set of synthetic oligodeoxyribonucleotide primers for DNA sequencing in the plasmid vector pBR322; Gene; 16(1-3); pp. 21-26; Dec. 1981.

Wang et al.; Plasmids in lactobacillus; Crit. Rev. Biotechnol.; 17(3); pp. 227-272; Jan. 1, 1997.

Weickert et al.; Genetic analysis of the promoter region of the bacillus subtilis alpha-amylase gene; J. Bacteril.; 171(7); pp. 3656-3666; Jul. 1989.

Wells et al.; Lactococcus lactis: high-level expression of tetanus toxin fragment c and protection against lethal challenge; Mol. Microbiol.; 8(6); pp. 1155-1162; Jun. 1993.

Wells et al.; Mucosal delivery of therapeutic and prophylactic molecules using lactic acid bacteria; Nat. Rev. Microbiol.; 6(5); pp. 349-362; May 2008.

White et al.; Transformations of quinic acid. Asymmetric synthesis and absolute configurations of mycosporin I and mycosporin-gly. The Journal of Organic Chemistry; 60(12); pp. 3600-3611; Jun. 1995.

White et al.; The synthesis and absolute configuration of micosporins. A novel application of the staudinger reaction. J. Am. Chem. Soc.; 111(24); pp. 8970-8972; Nov. 1989.

Yagur-Kroll et al.; Strategies for enhancing bioluminescent bacterial sensor performance by promoter region manipulation; Bioeng. Bugs; 1(2); pp. 151-153; Mar.-Apr. 2010.

Zhu et al.; Genetically engineered bacteria expressing alphaMelanocyte stimulating hormone alpha MSH as an inhibitor of traumatic ocular inflammatory reaction in rats; Invest. Opthalmol. Vis. Sci.; Apr. 2004; E-abstract-4005; retrieved from the internet http://abstracts.iovs.org/cgi/content/abstract/45/5/4005.

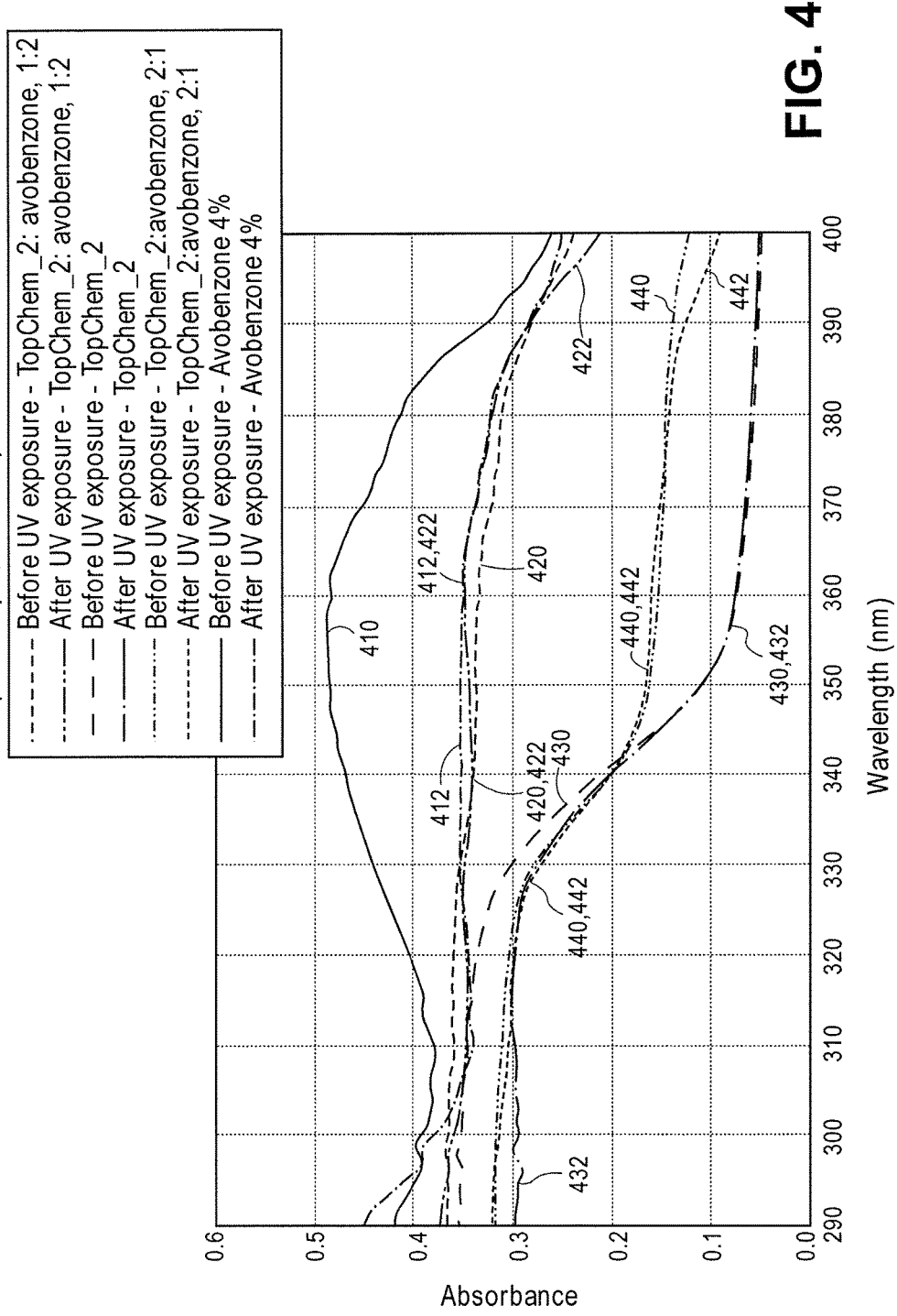

US 10,064,797 B2

TOPICAL FORMULATIONS FOR UV PROTECTION

CROSS-REFERENCE TO RELATED APPLICATIONS

This application claims priority to U.S. Provisional Application No. 62/013,276 filed on Jun. 17, 2014, entitled "Topical Formulations for UV Protection"; the disclosure of which is incorporated by reference.

TECHNICAL FIELD

The present disclosure is directed to novel active two-armed cyclic compounds which are capable of absorbing ultra violet (UV) radiation and protecting against sun damage, and their methods of production. Also described are topical compositions which are formulated to have a photo-protecting amount of the active compound when the composition is applied to skin of a subject.

BACKGROUND

Solar radiation has been shown to be harmful to human skin. Some harmful effects are seen immediately after sun exposure, such as in the case with sunburns, but in other cases, the damaging effects of solar radiation does not appear for many years post exposure.

Sun damage to the skin results from ultraviolet radiation (UVR) which reaches the surface of the earth. This UV radiation is divided in UVA and UVB. UVA (320 nm to 400 nm) contributes about 95% of the UVR, while UVB (290 nm to 320 nm) accounts for about 5%. Accordingly, topical sunscreens are formulated to contain active agents, which are able to absorb or reflect UVR having a wavelength of about 290 nm to 400 nm, and even reach beyond 400 nm into the visible spectrum at the blue light zone. These organic and physical sunscreens are classified into UV-A filters, UV-B filters, or broad spectrum filters (UV-A and UV-B functionality in a single molecule) depending on the type of radiation they absorb. UV-A sunscreens absorb radiation in the 320 to 400 nm regions of the ultra violet spectrum and UV-B sunscreens absorb radiation in the 290 to 320 nm regions of the ultra violet spectrum.

Topical sunscreen compositions are commonly used during outdoor work or leisure as a means for providing protection of exposed skin against acute and chronic adverse effects of solar radiation such as, for example, sunburn, sun exposure-related cancers, and skin photo-aging.

Many effective sunscreen preparations are sold commercially or are described in cosmetic or pharmaceutical literature. In general, sunscreen preparations are formulated as creams, lotions, sprays or oils containing as the active agent an ultra violet radiation absorbing chemical compound, or reflecting by physical compounds. As people have become more aware of the damaging effects of UVR, use of sunscreens has increased. Sun care products accounted for about 10% of the global skincare market in 2013 and the market is poised for growth of about 6.5% between 2013 and 2017. Global sun care sales reached about $8.7 billion in 2013. Research shows that consumers are highly concerned about sun damage, with 62% seeking sun protection benefits in skin care and body care products. Adding sun protection factor (SPF) to creams, lotions, and other body care products is becoming commonplace. Accordingly, it is desirable to improve sun protection formulations in terms of convenience, comfort and the duration of efficacy.

Currently, commercially available sun screen products are divided into two categories: chemical (organic) and physical. Chemical sunscreens are those which contain an active molecule which can absorb UVA and/or UVB radiation. Oxybenzone and avobenzone are examples of chemical sunscreens contained in sunscreen formulations. A pitfall of chemical sunscreens is the instability of the active ingredient when exposed to the sun. An example of a photosensitive sunscreen agent is avobenzone. Avobenzone becomes less effective as a sunscreen over time when exposed to solar radiation. Further, chemical compounds such as avobenzone degrade in the presence of some pigments, rendering the sunscreen ineffective. The mixing of chemical sun blocks with pigments can inadvertently occur when a user first applies such a sunscreen to her/his face followed by a cosmetic with pigments thereby rendering the active ingredient ineffective. Finally, some concerns have arisen regarding the safety of chemical sunscreens.

Physical sunscreens act as physical barriers which prevent UV rays to come into contact with a user's skin. Physical sunscreens primarily include titanium oxide or zinc oxide. Physical sunscreens, on the other hand, may generate free radicals that can be harmful. Further, physical sunscreens tend to be more visible. Both titanium oxide and zinc oxide type sunscreens come in a thick whitish paste that can be hard to apply and must be reapplied frequently as any sun-protecting qualities are lost when the physical layer of sunscreen is gone. Thus there exists a need for more natural sunscreen derivatives that can provide sun protection qualities and still be safe and relatively stable.

In recent years, a group of compounds known as mycosporines and mycosporine-like amino acids (MAAs) have received attention for their UV-absorbing qualities. Certain fungi produce mycosporine alone while cyanobacteria, algae, dinoflagellates, coral, and other marine organisms can produce both mycosporine and MAAs. MMAs are a family of intracellular compounds biosynthesized by the shikimate pathway for synthesizing aromatic amino acids involved in protecting aquatic organisms from solar radiation. MAAs are typically around 300 Daltons and are characterized by a cyclohexenon or cyclohexenimine chromophore. Discovered in the late 1960's, mycosporine and MAAs haven been subject of much research, and has been found to absorption range of 310 to 360 nm.

In recent years, some MAAs have received some attention as being viable sun screening agents. While MAAs have the benefit of being natural and thus less harmful than either chemical or physical sunscreens, the ability to produce and isolate enough MAAs from natural sources is time consuming and challenging. Thus, isolating enough MAAs from live organism to be placed into commercial production of sunscreen may not be economically feasible. Furthermore, attempts to produce MAAs synthetically has been unsuccessful thus far.

Disclosed herein are a new family of compounds with a two-armed cyclic structure and their syntheses, having some similarity to naturally-occurring MAAs by having a basic structure of amino acid cyclohexenone or cyclohexenimine conjugated arrangements. Yet, this family of molecules disclosed the feasible chemical structures and chemical variants that can absorb both UVA and UVB radiation. Thus, they are particularly effective and feasible as topical formulations for use as sunscreens. The sunscreen formulations described provide a stable active molecule and a topical formulation which is water soluble and provides greater comfort than current formulations when applied to the skin.

BRIEF DESCRIPTION OF THE DRAWINGS

FIG. 4 is a graph showing UV absorption spectra of TopChem2, avobenzone, TopChem2 and avobenzone at a 1:2 ratio, and Topchem2 and avobenzone at a 2:1 ratio before and after UV exposure.

SUMMARY

Figure 1:
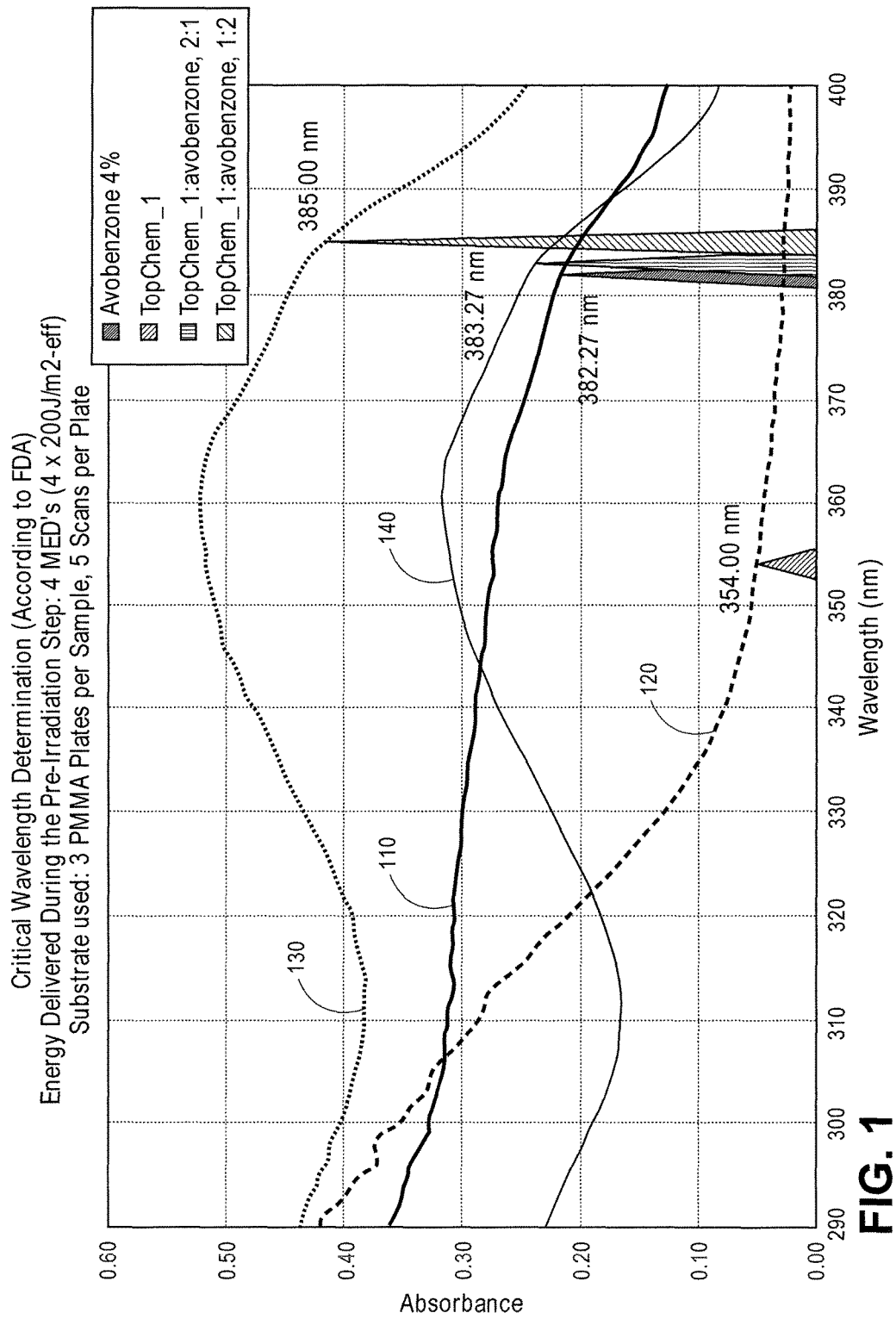
FIG. 1 is a graph showing UV absorption spectra of TopChem1, avobenzone, TopChem1 and avobenzone at a 1:2 ratio, and Topchem1 and avobenzone at a 2:1 ratio.

The present invention relates to compounds based upon naturally-occurring MAAs. The disclosed compounds having sun screening properties that can work independently or synergistically with existing sun screening agents. Also disclosed are synthetic pathways for making the disclosed compounds as well as formulations containing these compounds for use in a variety of products where having a sun screening agent is beneficial.

The examples and embodiments provided herein are intended to be illustrative and not exclusive. Those of skill in the art will recognize certain modifications, permutations, additions and sub-combinations thereof as an intended part of the instant disclosure. Additional features will become apparent to those of skill in the art upon a reading of the specification and a study of the structures provided.

In one aspect, a two-armed cyclic compound is provided having the general formula (I):

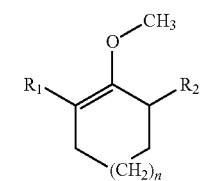

(I)

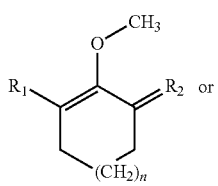

IA

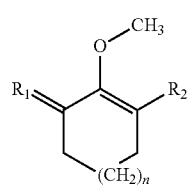

IB wherein:
$R_1$ is: $=O$, $-OH$, $-NH$, $-CH_2-COO^-$, $-NH-CH_2-COO^-$,

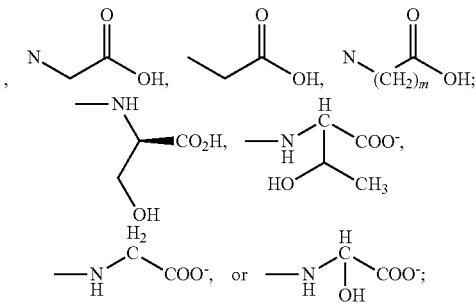

$R_2$ is: $=O$, $-OH$, $-NH$, $-CH_2-COO^-$, $-NH-CH_2-COO^-$,

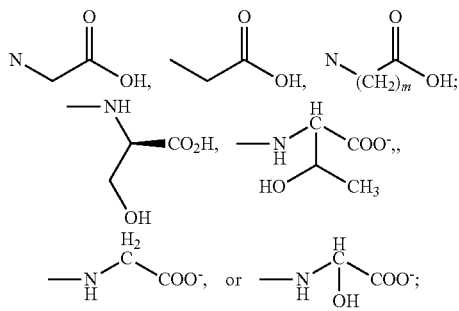

n=1, 2, 3 or 4; and
m=1, 2, 3, 4, 5, 6, 7, 8 or 9;
wherein $R_1$ or $R_2$ is

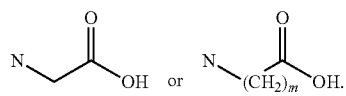

In one embodiment, $R_1$ and $R_2$ are the same. In another embodiment, $R_1$ and $R_2$ are different.

In a specific embodiment related to the foregoing, $R_1$ and $R_2$ are both

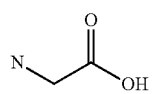

and $R_2$ is

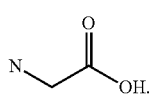

In another embodiment, $R_1$ and $R_2$ are different.
In one embodiment, the compound of formula (I) has the structure selected from the group consisting of:

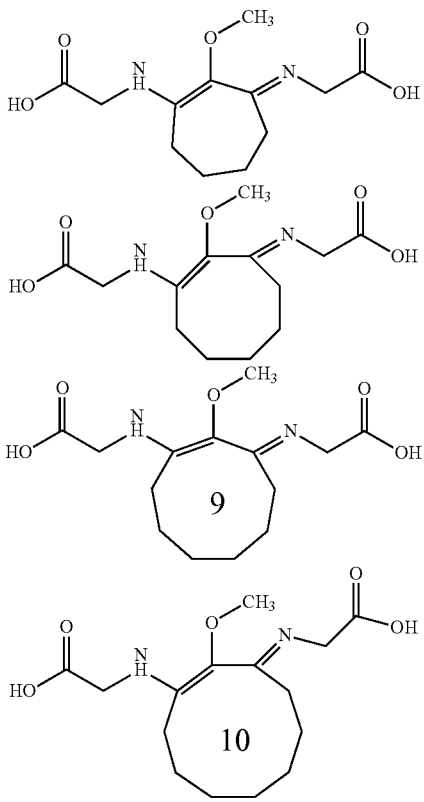

In another aspect, a two-armed cyclic compound is provided having the general formula (II):

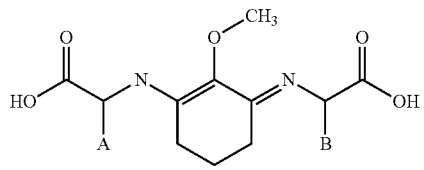

(II)

wherein A and B are each H.

In one embodiment, the two-armed cyclic compound has the general formula II wherein A is H, a methyl group, or CH(R)COOH, wherein R is H or an alkyl group containing 1 to 3 carbons which are optionally substituted by a hydroxyl group or an ester thereof; and B is a methyl group, or CH(R)COOH, wherein R is H or an alkyl group containing 1 to 3 carbons which are optionally substituted by a hydroxyl group or an ester thereof.

In another aspect, a compound of formula (III) is provided:

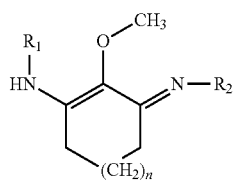

(III)

where n is selected from 0, 1, 2, 3, and 4,
$R_1$ and $R_2$ are each independently $-(CH_2)_m-COOH$ or $-(CH_2)_y-CH(A)-COOH$, where
m is an integer ranging from 1-9,
y is an integer ranging from 0 to 8,
A is a C1-C3 linear or branched alkyl or alkenyl optionally substituted at one or more carbon atoms with hydroxy or $-C(O)OR_3$, where R3 is an ester, and when C taken together with A forms a double bond, the H in CH(A) is absent.

In one embodiment, n is 1.
In one embodiment, n is 2.
In one embodiment, n is 3.
In one embodiment, n is 4.
In one embodiment, $R_1$ and $R_2$ are each independently selected from $-CH_2-COOH$, $-(CH_2)_2-COOH$, $-(CH_2)_3-COOH$, $-(CH_2)_4-COOH$, $-(CH_2)_5-COOH$, $-(CH_2)_6-COOH$, $-(CH_2)_7-COOH$, $-(CH_2)_8-COOH$, and $-(CH_2)_9-COOH$.
In one embodiment, y is 0.
In one embodiment, y is 1.
In one embodiment, A is selected from the group consisting of $-OH$, $-CH_3$, $-CH_2CH_3$, $-CH_2CH_2CH_3$, $-CH_2OH$, $-CH(CH_3)_2$, $-CHCH_3OH$.
In one embodiment, $R_1$ and $R_2$ are each independently selected from the group consisting of:

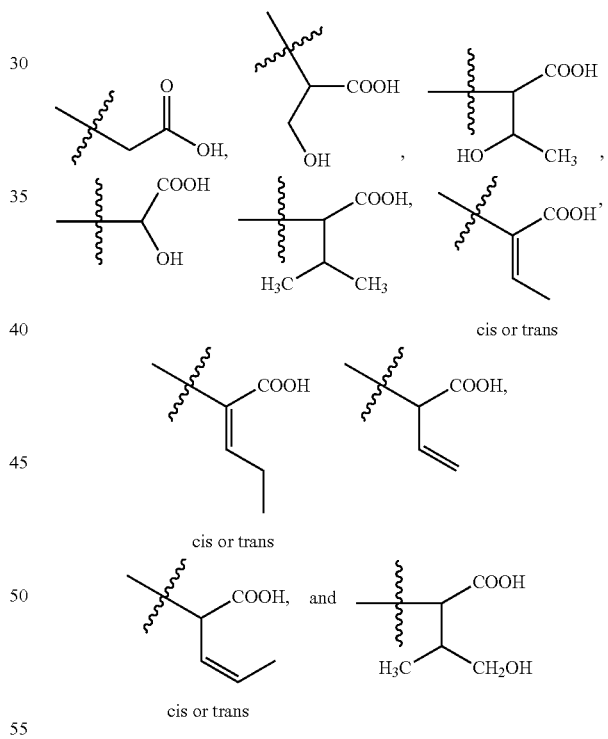

In one embodiment, $R_1$ and $R_2$ are the same.
In one embodiment, $R_1$ and $R_2$ are different.
In another aspect, a composition for topical administration comprising the two-armed cyclic compound of formula (I), (II) or (III) which is photoprotecting and a pharmaceutically acceptable excipient.
In one embodiment, the composition is a water-in-oil emulsion comprising the compound of formula (I), (II) or (III). In another embodiment, the composition is an oil-in-water emulsion comprising the compound of formula (I), (II), or (III).

In one embodiment, the composition further comprises one or more additional compounds which absorb UV radiation. In another embodiment, the composition further comprises titanium oxide or zinc oxide. In yet another embodiment, the composition further comprises avobenzone.

In one embodiment, the composition for topical administration retains at least 50%, 90% or 95% of its UV absorbance after being irradiated with 4 MEDs (Minimal Erythema Doses) of energy from a simulated solar radiation source.

In another embodiment, the UV absorbance by the topical administration is over the range of 290 nm to 400 nm, 300 nm to 390 nm, 310 nm to 400 nm, 320 nm to 400 nm, 310 nm to 380 nm, 310 nm to 370 nm or 310 to 365 nm.

In another aspect, a method for protection against sunburn or sun damage is provided, comprising topically administering a composition comprising the compound of formula I, formula II or formula III.

In one embodiment, the composition is formulated to be a liquid (liniment, solutions, emulsions, suspensions, aerosols), or a semi-solid (such as creams, lotions, gels, pastes, ointments, jellies), or a solid (such as powder, aerosol, plaster).

In one embodiment, the composition is formulated with additional ingredients to provide a commercial product. Examples of such additional ingredients are binders, stabilizers, emollients, penetration enhancers, surfactants, fragrance, and the like.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

"Erythema" is a non-specific term used to define the redness of the skin produced by a congestion of the capillaries that can result from a variety of causes. Erythema can be cause in the skin by, among other things, friction, irritation and exposure to UV, visible and infrared radiation. "Sunburning" or "sunburn" is defined as an injury to the skin with erythema, tenderness and sometimes painful blistering, following excessive overexposure to UV radiation.

"Minimal Erythema Dose" (MED) is defined herein as the threshold dose of UV radiation that may produce sunburn. MED may also be defined as the time of exposure that produces that minimally perceptible erythema at 16 to 24 hours post-exposure. MED may be measured for UVA and/or UVB radiation.

"Pharmaceutically acceptable salt" refers to a biologically compatible salt of a compound that can be used as a drug, which salts are derived from a variety of organic and inorganic counter ions well known in the art.

"Pharmaceutically effective amount" or "therapeutically effective amount" refers to an amount of a compound sufficient to treat a specified disorder or disease or one or more of its symptoms and/or to prevent the occurrence of the disease or disorder. "Treatment" includes arresting further advancement of a disease, as well as reversing the disorder, inducing regression of lesions, or in some examples curing the disorder.

"Subject" refers to humans and non-human subjects, and includes all mammals.

"Topical" delivery refers to application of a drug-containing formulation to the skin to directly treat cutaneous disorders or the cutaneous manifestations of a disease with the intent of substantially directing the pharmacological effect of the drug to the surface of the skin or within the skin. Topical dosage forms are typically semi-solid systems, but can include a variety of other dosage forms such as foams, sprays, medicated powders, solutions and medicated adhesive systems. Topical delivery includes external topical agents that are spread, sprayed, or otherwise dispersed on cutaneous tissues to cover the affected area, or internal topical agents that are applied to the mucous membranes orally, vaginally, or on anorectal tissues for local activity. The topical drugs disclosed herein can be administered in any topical dosage form, for example as a solid (powder, aerosol or plaster); liquid (lotion, liniment, solution, emulsion, suspension, aerosol) or semi-solid (ointment, cream, paste, spray, gel, jelly or suppository).

"Topical base" refers to the solid component of a topical formulation. A therapeutically effective amount of an active compound is combined with a topical base to produce a topical formulation such as an ointment, a cream, spray or a lotion. The topical formulation also may include additional components such as excipients, including, without limitation, antioxidants, binders, emollients, penetration enhancers, surfactants, and the like.

"Photoprotecting effective amount" as used herein refers to the amount of a compound as disclosed herein which absorbs UV radiation. A composition comprising a photoprotecting effective amount will reduce or prevent erythema or reddening of skin to which the composition is applied as compared to the erythema or reddening of the skin to which the composition has not been applied. A photoprotecting effective amount of the composition, when applied to the skin of a subject, will increase the Minimal Erythema Dose (MED) by at 10%, 25%, 50%, 75%, or 95% as compared to the MED for skin of the subject which to which the composition has not been applied. MED may be used to indicate photoprotecting effective amounts of a composition upon exposure to UVA, UVB, or both UVA and UVB radiation.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

II. In Vitro Determination of SPF

SPF can be determined in vitro using the following protocol. Samples of the topical formulation containing the compound of Formula (I) is applied to PMMA (poly(methylmethacrylate)) plates (Schongerg, Hamburg, Germany) as a film at a concentration of 2 mg/cm$^2$. Controls are also utilized in which: 1) no topical formulation is applied to the PMMA and 2) the topical formulation containing none of the compound of Formula (I) is applied to the PMMA.

The samples of the composition are irradiated with simulated natural sunlight to 15 MEDs (minimal erythemal dose) emitted by a Solar Light Model ISS Xenon Arc Solar Simulator equipped with Solar Light Dose Control System and UVB detector. The Solar Simulator is calibrated to meet the common international SPF methodology jointly promulgated by the European Cosmetics Association ("COLIPA"), the Japan Cosmetic Industry Association, the Cosmetic, Toiletry and Fragrance Association of South Africa, published on May 2006, referred to herein as the "COLIPA standard." The dose control and detector systems are also calibrated. The amount of energy transmitted through the composition is recorded initially and then at intervals until 15 MEDs have been administered. The SPF at each interval is calculated by dividing the amount of energy transmitted through a blank film by the amount transmitted through the product-coated film.

III. In Vivo Determination of SPF

To determine the SPF of the topical formulation containing the compound of Formula (I), test sites on human subjects are used. A test site area serves as an area for determining the subject's Minimal Erythema Dose (MED) after application of either the sunscreen product or for determining the subject's MED of unprotected skin (control site). Each subject's MED is the time of exposure that produces that minimally perceptible erythema at 16 to 24 hours post-exposure. A test site on the back of each subject is designated between the beltline and the shoulder blades and lateral to the midline. Responses on unprotected skin (no test material applied) and protected skin (sunscreen test product(s) or SPF standard is applied) are determined at separate unprotected and protected test sites, respectively. Test sites are randomly located in a blinded manner. Each test site is a minimum of 30 square centimeters and outlined with indelible ink.

Within each test site are about 5-8 test subsites, each having an area of at least about 0.5 cm$^2$ and separated from each other by at least about 0.8 cm. Each test subsite is outlined with indelible ink.

The test topical formulation or control composition is applied to each test site at a 2 mg/cm$^2$. A finger cot compatible with the formulation is used to spread the product as evenly as possible. After a waiting period of at least and about 15 minutes, the test sites are exposed to UV radiation.

A series of UV light exposure (units of time) are administered to the subsites on each subject with the solar simulator. One series of exposures is administered to the untreated, unprotected skin to determine the MED. The MED is the time of exposure that produces the minimally perceptible erythema at 16 to 24 hour post-exposure. The MED of the subject's unprotected skin is determined prior to the test day, then again on the test day.

Each of the protected test sites (controls and/or test sunscreen product) are also exposed to UV light. The standard time intervals selected are a geometric series represented by (1.25)n, wherein each exposure time interval is 25 percent greater than the previous time. (The reason for using the geometric sequence of UV exposure is to maintain the same relative uncertainty, expressed as a constant percentage), independent of the subject's sensitivity to UV light, regardless of whether the subject has a high or low MED). The exact series of exposures to be given is determined by the MED of the unprotected skin.

Each subject reports back at 16 to 24 hours post-exposure, at which time each test site area is read to determine the Minimal Erythema Dose (MED) of both the unprotected and the protected skin. The SPF of the test sunscreen is then calculated from the exposure time interval required to produce the MED of the protected skin, and from the exposure time interval required to produce the MED of the unprotected skin (control site), i.e., $$SPF = \frac{MED \text{ Protected Skin}}{MED \text{ Unprotected Skin}}$$

A topical composition which has a photoprotecting effective amount of the active compound will have an SPF of at least about 15.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

IV. Mycosporine and Mycosporine-Like Amino Acids (MAAs) and their Analogs

A number of photosynthetic microorganisms which are exposed to visible and UV radiation have evolved mechanisms to circumvent the damaging effects of UV radiation. One of these mechanisms is the synthesis of UV-absorbing or screening compounds. The most well-known natural UV-absorbing compounds are mycosporines and mycosporine-like amino acids (MAAs). They are low molecular weight, water-soluble molecules which absorb UV radiation having a wave length between about 310 and 365 nm. These are found in many cyanobacteria and possibly in other prokaryotes, and in eukaryotes such as microalgae, yeast and fungi. A review of several MAAs and their structures can be found, for example, in Llewellyn and Airs (*Mar. Drugs*, 2010, 8:1273-1291).

Much research on the topic of mycosporine and MAAs have been directed towards understanding their mechanism of synthesis within their corresponding organism and attempting to derive these UV absorbing compounds via biological means. In those cases, the hope has been to discover a viable way to easily produce these compounds for commercial use. Unfortunately thus far, a feasible means of production reasonable amounts of MAAs biologically is still lacking. As a result, commercial products containing biologically-derived MAAs are expensive and few and far in between.

Research efforts have also been geared towards finding synthetic ways of making MAA compounds. Researchers focused on finding such synthetic means of making MAAs have also been confounded by its complexity. To date, there does not appear to exist any literature on a synthetic method for producing such MAAs. The difficulty with synthesizing MAAs from available compounds likely stems from the chirality of naturally-occurring MAAs. As with other chiral compounds, being able to control which enantiomer one has in each of the synthesis steps is challenging. Thus, it was surprising here that by synthesizing molecules similar to naturally-occurring MAAs but omitting the chiral center of naturally-occurring MAAs, that the resulting compounds still maintain a certain level of UV absorption.

Herein disclosed are novel compounds having a two-armed cyclic structure which can absorb both UVA and UVB radiation and which, when formulated as a topical composition, can protect against sun damage, sunburn, and/or erythema.

V. The Two-Armed Cyclic Compound

The two-armed cyclic compounds in accordance with the present disclosure correspond to formula (I) below:

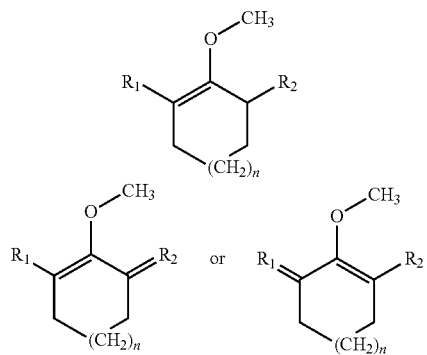

wherein:
$R_1$ is

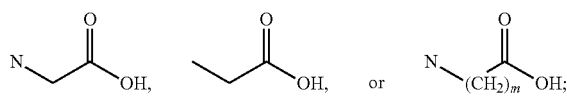

$R_2$ is

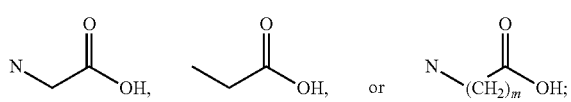

n=1, 2, 3 or 4; and
m=1, 2, 3, 4, 5, 6, 7, 8 or 9;
wherein when $R_1$ or $R_2$ is

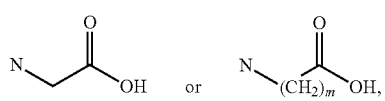

the bond between the N and the aromatic ring is a double bond.

In some embodiments, $R_1$ is the same as $R_2$. In other embodiments, $R_1$ is different than $R_2$.

Among the compounds of formula (I), more particularly exemplary are the following:

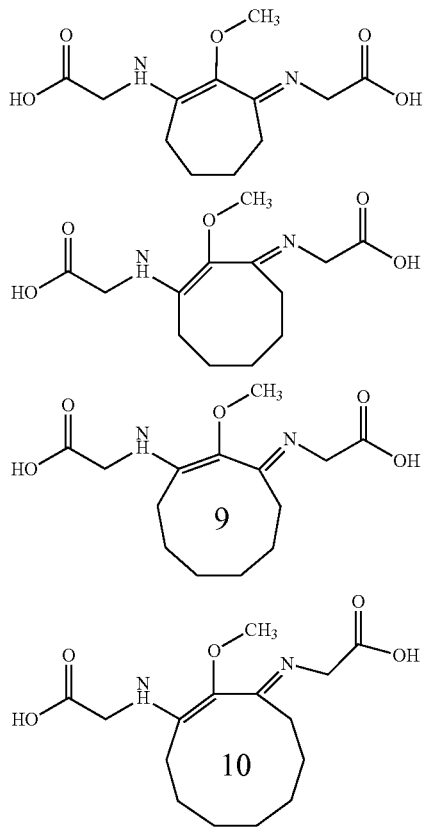

In another embodiment, the two-armed cyclic compounds correspond to formula (II) below:

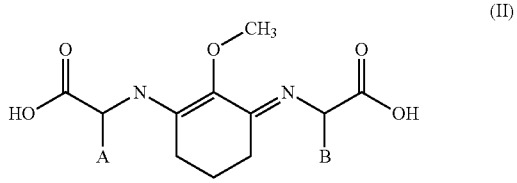

wherein
A is H, $CH_3$ or CH(R)COOH, wherein R is H or an alkyl group comprising 1, 2 or 3 carbons; and
B is H, $CH_3$ or CH(R)COOH, wherein R is H or an alkyl group comprising 1, 2 or 3 carbons.

In some embodiments, A is the same as B. In other embodiments, A is different than B.

In some embodiments, R is substituted by a hydroxyl or ester group.

In some embodiments, a CTA as described herein can also be synthesized starting with two non-cyclic molecules such as:

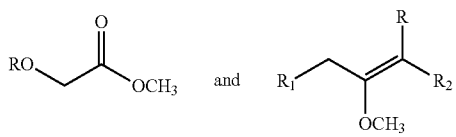

One of ordinary skill in the art will appreciate that the compound of formula (I) may exhibit the phenomena of tautomerism, conformational isomerism and/or geometric isomerism. It should be understood that the invention encompasses any tautomeric, conformational isomeric and/or geometric isomeric forms of formula (I) as well as mixtures of these various different isomeric forms. The invention also is meant to encompass atropisomers. Formula (I) may be in the form of a salt. Such salts include salts suitable for pharmaceutical uses ("pharmaceutically-acceptable salts"), salts suitable for veterinary uses, and the like. Such salts may be derived from acids or bases, as is well-known in the art.

VI. Compounds and Compositions

Contained herein are studies on two of the compounds derived from the base structure shown above: 3-hydroxy-2-methoxy-cyclo-2-enone and 2-methoxy-cyclohex-2-enone-3-amino acetic acid. In both cases, the absorptivity of these two compounds were studied. In addition, photostability of these two compounds were also assessed by taking a second UV absorption spectra after exposing the compounds to UV. Photostability of sun screening compounds are of critical importance as a compound would be completely ineffective if they lose their UV absorptive qualities shortly after being exposed to solar radiation. In addition to identifying compounds that are UV absorbers, it was also discovered that combining the novel compounds with various chemical and physical known UV absorbing and reflecting compounds had a surprising effect of increasing the overall absorption capabilities of the resulting composition as well as being more stable when exposed to UV light.

Turning to FIG. 1, the absorption spectra for 3-hydroxy-2-methoxy-cyclo-2-enone absorbs most strongly around 262 nm but its absorbance drops off by approximately half at 320 nm. A first spectrum 110 is shown for avobenzone. Avobenzone is an example for a known chemical UV absorber that can be combined. A second spectrum 120 is for 3-hydroxy-2-methoxy-cyclo-2-enone (labeled TopChem_1 in the drawing). A third spectrum 130 is a spectrum corresponding to a ratio of 3-hydroxy-2-methoxy-cyclo-2-enone to avobenzone of 1:2. And a fourth spectrum 140 is spectrum corresponding to a ratio of 3-hydroxy-2-methoxy-cyclo-2-enone to avobenzone of 2:1.

Staying with FIG. 1, while both 3-hydroxy-2-methoxy-cyclo-2-enone and avobenzone had relatively low 320 nm and 400 nm, the combination of 3-hydroxy-2-methoxy-cyclo-2-enone and avobenzone, especially at a 1:2 ratio of 3-hydroxy-2-methoxy-cyclo-2-enone with avobenzone provided substantial UV absorption between 320 nm and 390 nm. The increase in UV absorptive abilities of the combined compounds is surprising because it surpasses the additive effects of each compound singularly and provides for UV absorption at a wavelength range that would be considered poor for each compound alone.

Figure 2:
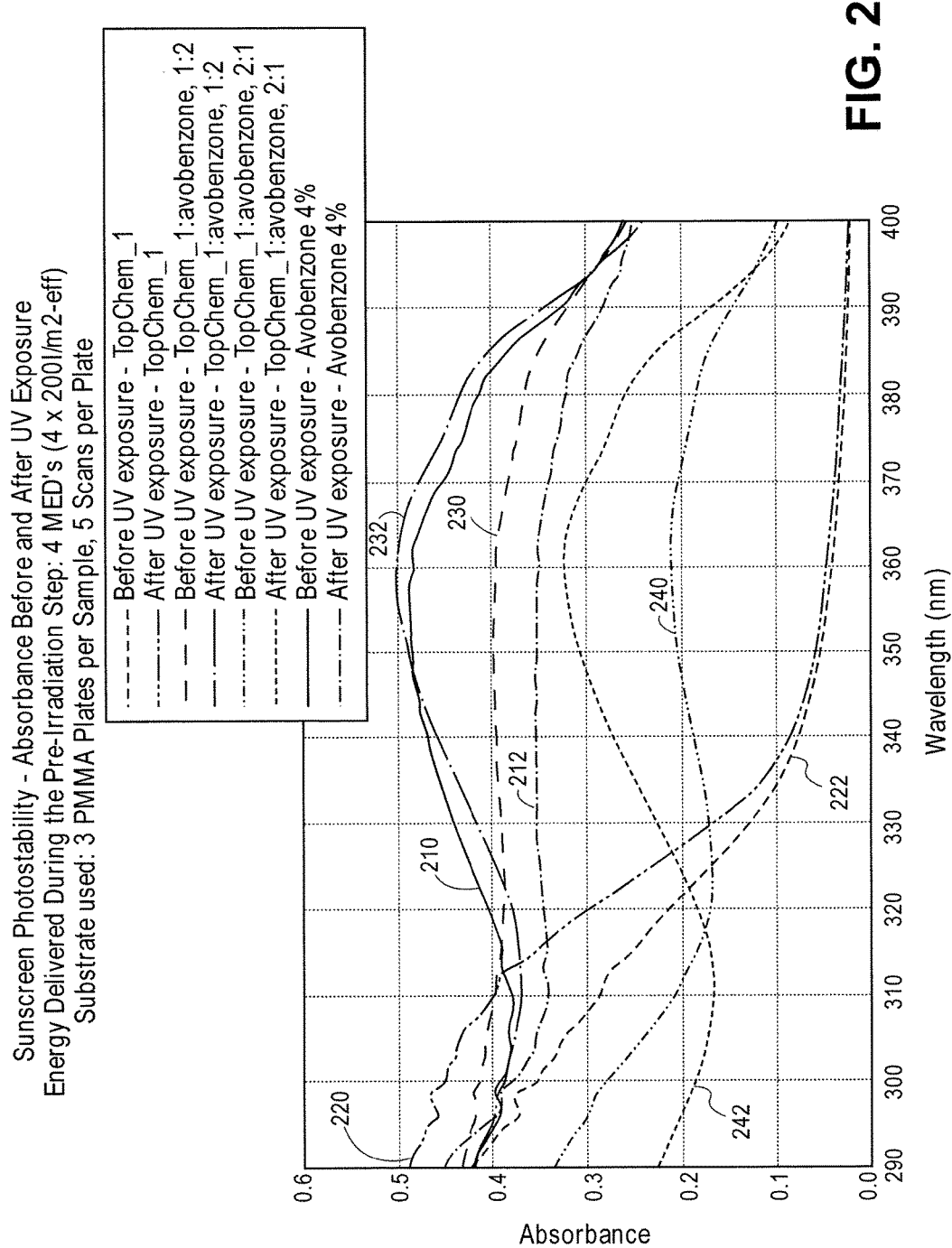
FIG. 2 is a graph showing UV absorption spectra of TopChem1, avobenzone, TopChem1 and avobenzone at a 1:2 ratio, and Topchem1 and avobenzone at a 2:1 ratio before and after UV exposure.

Turning to FIG. 2, this set of spectra show the effects of UV exposure on 3-hydroxy-2-methoxy-cyclo-2-enone, avobenzone, and combinations thereof over a wavelength range of 290 nm and 400 nm. A first spectrum 210 and a second spectrum 212 are for avobenzone before and after UV exposure. A third spectrum 220 and a fourth spectrum 222 are for 3-hydroxy-2-methoxy-cyclo-2-enone before and after UV exposure, respectively. A fifth spectrum 230 and a sixth spectrum 232 correspond to a combination of 3-hydroxy-2-methoxy-cyclo-2-enone and avobenzone at a ratio of 1:2 before and after UV exposure, respectively. Finally, a seventh spectrum 240 and an eighth spectrum 242 correspond to a combination of 3-hydroxy-2-methoxy-cyclo-2-enone and avobenzone at a ratio of 2:1 before and after UV exposure, respectively.

While both 3-hydroxy-2-methoxy-cyclo-2-enone and avobenzone on their own behaved as expected where after UV exposure, their respective UV absorptive abilities dropped overall, but most dramatically within the wavelength ranges where they were most absorptive prior to UV exposure, the UV absorption of the combined compounds at both the 1:2 and 2:1 ratio increased after UV exposure. This was especially surprising for the composition containing a 1:2 ratio of 3-hydroxy-2-methoxy-cyclo-2-enone and avobenzone.

Figure 3:
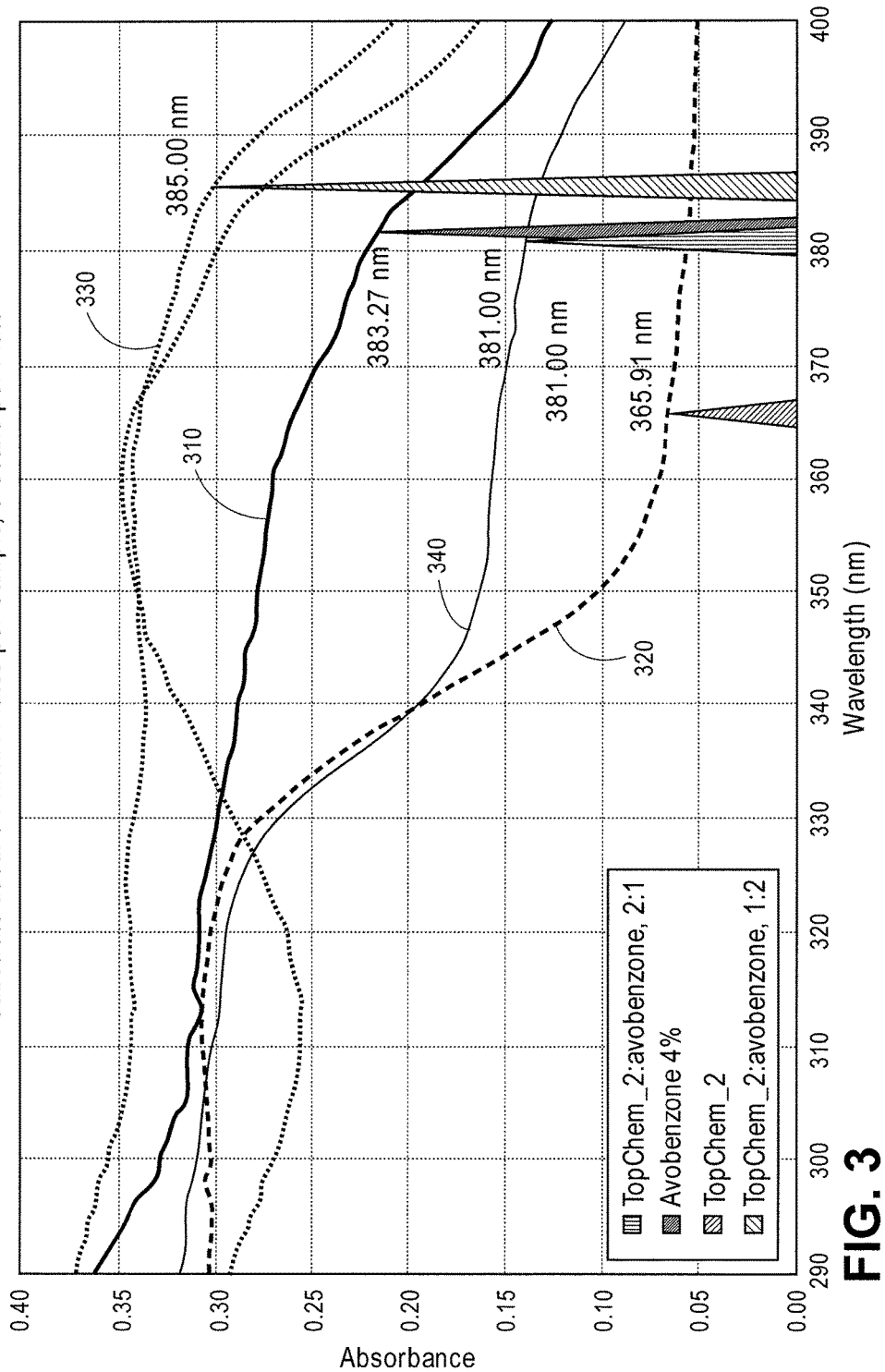
FIG. 3 is a graph showing UV absorption spectra of TopChem2, avobenzone, TopChem2 and avobenzone at a 1:2 ratio, and Topchem2 and avobenzone at a 2:1 ratio.

Next, similar tests were performed on 2-methoxy-cyclohex-2-enone-3-amino acetic acid and can be seen in FIGS. 3 and 4. In FIG. 3, a first spectrum 310 is shown for avobenzone. A second spectrum 320 is for 2-methoxy-cyclohex-2-enone-3-amino acetic acid (labeled TopChem_2 in the drawing). A third spectrum 330 is a spectrum corresponding to a ratio of 2-methoxy-cyclohex-2-enone-3-amino acetic acid to avobenzone of 1:2. And a fourth spectrum 340 is spectrum corresponding to a ratio of 2-methoxy-cyclohex-2-enone-3-amino acetic acid to avobenzone of 2:1.

2-methoxy-cyclohex-2-enone-3-amino acetic acid absorbs most strongly at a wavelength of 302 nm and maintains a fairly steady absorption pattern for the entire range of wavelengths between 290 nm and 400 nm. Similar to results for 3-hydroxy-2-methoxy-cyclo-2-enone and avobenzone, the combination of 2-methoxy-cyclohex-2-enone-3-amino acetic acid with avobenzone at a 1:2 ratio increased the UV absorptive qualities of the composition to greater than that for 2-methoxy-cyclohex-2-enone-3-amino acetic acid and avobenzone alone.

FIG. 4 shows the photostability of 2-methoxy-cyclohex-2-enone-3-amino acetic acid and avobenzone alone and in combination. This set of spectra show the effects of UV exposure on 2-methoxy-cyclohex-2-enone-3-amino acetic acid, avobenzone, and combinations thereof over a wavelength range of 290 nm and 400 nm. A first spectrum 410 and a second spectrum 412 are for avobenzone before and after UV exposure. A third spectrum 420 and a fourth spectrum 422 are for 2-methoxy-cyclohex-2-enone-3-amino acetic acid before and after UV exposure, respectively. A fifth spectrum 430 and a sixth spectrum 432 correspond to a combination of 2-methoxy-cyclohex-2-enone-3-amino acetic acid and avobenzone at a ratio of 1:2 before and after UV exposure, respectively. A seventh spectrum 440 and an eighth spectrum 442 correspond to a combination of 2-methoxy-cyclohex-2-enone-3-amino acetic acid and avobenzone at a ratio of 2:1 before and after UV exposure, respectively. Finally, where overlaps in different spectra occur, multiple number are noted for a particular segment of the spectra. For instance, at a wavelength between 360 nm and 370 nm, the second spectrum 412 for UV exposed avobenzone and the fourth spectrum 422 for UV exposed 2-methoxy-cyclohex-2-enone-3-amino acetic acid overlap at that range as indicated by the two numbers pointing to that segment of spectra.

The results of this photostability test remain consistent with the previous findings that combining avobenzone with the chemically synthesized molecules of this invention causes the composition to retain its UV absorptive qualities and in some instances, has the potential to increase the UV absorptive qualities to greater than each of the components on their own.

The results from testing both 3-hydroxy-2-methoxy-cyclo-2-enone and 2-methoxy-cyclohex-2-enone-3-amino acetic acid bring promise that other chemically synthesized compounds lacking the chiral center of naturally occurring MAA will behave similarly when combined with other UV absorbing compounds in addition to avobenzone. The formulations outlined above may be combined with other known UV absorbers and/or reflectors such as Avobenzone, Benzophenones, Cinoxate, Dioxybenzone, Menthyl anthranilate, Octyl methoxycinnamate, Octyl salicylate, Padimate O, Phenylbenzimidazole sulfonic acid, Sulisobenzone, Titanium dioxide, Trolamine salicylate, TEA salicylate, Zinc oxide, Ensulizole, Meradimate, Octisalate, amiloxate, bemotrizinol, Bemotrizinol-bis-ethyihexyloxyphenol methoxyphenyl, bisoctrizole, diethylhexyl butamido triazone, drometrizole trisiloxane, ecamsule, enzacamene, octyl triazone, ACETAMINOPHEN, octylcrylene, octinoxate, octisalate, oxybenzone, homosalate, Heliopex, 4-MBC, Mexoryls-terephthalylidene dicamphor sulfonic acid: mexoryl SX and XL, Tinosorb S and M, Uvinul T 150, styrene/acrylate copolymer, Phenylethyl Benzoate, calcium aluminum borosilicate/sodium borosilicate beads and Uvinal A Plus, and derivatives of thereof. Furthermore, a natural extension from the results of the novel compounds described herein with avobenzone can also be extended to physical sun screens and/or reflectors such as titanium oxide and zinc oxide.

Next, the class of compounds that belong to Formulation (I), Formulation (II), and Formulation (III) are expected to absorb at wavelengths that will vary with the 290 nm to 400 nm range. For example, 2-methoxy-3-(imino glycine) cyclohex-1-ene-amino acetic acid and 2-methoxy-3-{(4-methoxyphenyl) imino} cyclohex-1-ene amino acetic acid have their maximum absorption at 327 nm and 337 nm, respectively. It is quite likely that when, 2-methoxy-3-(imino glycine) cyclohex-1-ene-amino acetic acid and 2-methoxy-3-{(4-methoxyphenyl) imino} cyclohex-1-ene amino acetic acid, when combined with a second UV absorber will shift the maximum absorbing wavelength to a longer wavelength as was the case with 3-hydroxy-2-methoxy-cyclo-2-enone and 2-methoxy-cyclohex-2-enone-3-amino acetic acid. Having compounds that absorb at these greater wavelengths is especially advantageous as sunscreen coverage of the UVA range (315 nm to 400 nm) by commercially available sunscreens is inadequate.

Along the same lines as mentioned in the previous paragraph, it is possible then to select for certain wavelength ranges by selecting the R1 and R2 groups that are present in the compound as well as varying the R1 and R2 groups of the compounds within the composition. This also brings up the possibility of compositions of UV absorbing agents derived from a combination of compounds contained with Formulation (I), Formulation (II), and Formulation (III). It appears that unlike other UV absorbers that degrade in the presence of other UV absorbers, these novel compounds, when combined, actually possess higher UV absorbing characteristics.

VII. Topical Formulations

The compositions according to the disclosure may be formulated for topical administration according to techniques that are well known to one skilled in this art. Without intending to be limiting, but for the purposes of exemplary embodiments, it is contemplated that the topical formulation may be a gel, ointment, lotion, emulsion, cream, foam, mousse, liquid, spray, suspension, dispersion or aerosol. The formulation includes one or more excipients to provide the desired form and a desired viscosity, flow or other physical or chemical characteristic for effective application, coverage and adhesion to the skin.

Excipients in the formulation are selected based on the type of formulation intended. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinyl alcohol, polyvinylpyrrolidone, sugars, and starches.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA (hydrofluoroalkane) propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", 4th Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product.

Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type." Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams and mousses consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal. In one embodiment, a concentration of a preservative that is effective to prevent fungal growth is selected, without affecting the effectiveness of the composition for its intended purposed upon topical application.

VIII. Physical Sunscreens

Sunscreens are broadly classified into two categories, i.e., chemical sunscreens and physical sunscreens. Unlike chemical sunscreens which comprise a UV-absorbing agent such as described above, physical sunscreens act by physically blocking radiation. Many sunscreen compositions have a combination of ingredients and may contain both physical and chemical sunscreens. Physical sunscreens include e.g., titanium dioxide and zinc oxide, and block both UVA and UVB radiation. In a first embodiment, a composition is herein envisioned in which a physical sunscreen composition is formulated to include one or more UV-absorbing agents described above, including that of formula (I), formula (II) or formula (III), when a physical sunscreen is part of formula (I), formula (II), or formula (III), and/or the physical sunscreen exist in the final formulation with formula (I), formula (II), or formula (III).

IX. Combination Formulations

Optimizing protection from UV radiation is sometimes best done through the use of a topical composition containing one, two, three or more UV-absorbing compounds. Therefore, variations on the presently disclosed compositions include a combination of at least one novel two-armed cyclic molecule as described herein and another UV-specific compound to absorb or block UVA and/or UVB radiation to protect the skin. These compounds, alone or in combination, filter a percentage of the UV spectrum depending on the type, concentration, and intensity of chromophores used.

The filter families include, alone or in combination, and not limited to, the benzotriazoles, benzophenones, benzoic acids/PABA, cinnamates, salicylates, and avobenzones, to further protect the skin against UVA and UVB damage. Maximum loads of one or more UV filters present in a sunscreen composition can be up to 15-50% by weight. A UVA and UVB filter, individually, are present in an amount of about 0.25 to about 10%, 0.5 to 8%, 1 to 7.5%, 2 to 5% or 0.5 to 5% percent by weight of the composition. When both a UVA and UVB blocker are used, each typically is present in an amount of about 0.5 to about 10, 0.5 to 8%, 1 to 7.5%, 2 to 5% or 0.5 to 5% percent, by weight. Physical sunscreens are presented in amounts as high as 10%, 20%, 25% or 30%.

Examples of chemical sunscreens include: oxybenzone (benzophenone-3), tannic acid, uric acids, quinine salts, dihydroxy naphtholic acid, an anthranilate, phenylbenzimidazole sulfonic acid, and PEG-25 PABA. Further, sunscreen compounds such as dioxybenzone, cinoxate, ethyl 4-[bis (hydroxypropyl)]aminobenzoate, glyceryl aminobenzoate, homosalate, menthyl anthranilate, octocrylene, octyl methoxycinnamate, octyl salicylate, padimate A, padimate 0, red petrolatum, titanium dioxide, 4-menthylbenzylidene camphor, benzophenone-1, benzophenone-2, benzophenone-4, benzophenone-6, benzophenone-12, isopropyl dibenzoylmethane, butyl methoxydibenzoylmethane, zotocrylene, DEA-methoxycinnamate, digalloyl trioleate, TEA-salicylate, or zinc oxide can be used in the present composition.

Additional UV filters, including combinations of any two or more, are selected from the following categories (with specific examples): p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3 benzylidene, 4 methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxynaphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, octabenzone, 4-isopropyldibenzoylmethane, butylmethoxydibenzoylmethane, etocrylene, and 4-isopropyl-dibenzoylmethane).

In another embodiment, the composition envisioned can also include at least one chemical sunscreen component such as one selected from the list above. It would also be reasonable to include greater than one chemical sun blocking component to broaden the wavelength coverage profile of the overall composition. Evidence of increased photostability and increased UV absorptive characteristics from a combination formulation has been shown here. Furthermore, it is also conceived that the composition includes a combination of compounds having chemical structures found in Formula (I), Formula (II), and/or Formula (III).

X. Additional Components

The compositions of the invention can further include components such as insect repelling components. The most widely used insect repelling active agent for personal care products is N,N-Diethyl-m-toluamide, frequently called "DEET" and available in the form of a concentrate containing at least about 95 percent DEET. Other synthetic chemical repellents include ethyl butylacetylaminoproprionate (also known as IR 3535), dimethyl phthalate, ethyl hexanediol, indalone, di-n-propylisocinchoronate, bicycloheptene, dicarboximide and tetrahydrofuraldehyde. Certain plant-derived materials also have insect repellent activity, including citronella oil and other sources of citronella (including lemon grass oil), limonene, rosemary oil and eucalyptus oil. Choice of an insect repellent for incorporation into the sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

Yet another component that can be included in the compositions thus far described are natural components that aim to sooth the skin. Having natural components that help soothe and potentially protect the user's skin while wearing the composition under sun exposure can be beneficial to the user's skin health. Natural components include but are not limited to, aloe, witch hazel, willow bark, bromelain, turmeric, and chamomile.

XI. Protection from Ultraviolet Radiation

The compounds of the present disclosure are effective in absorbing UV radiation in the range of 290 nm to 400 nm. In alternative embodiments, one or more of the compounds absorbs UV radiation in the range of 300 nm to 390 nm, 310 nm to 400 nm, 320 nm to 400 nm, 310 nm to 380 nm, 310 nm to 370 nm, or 310 to 365 nm. Accordingly, when a topical composition is formulated to comprise the protective compound as described above, the topical composition will protect a subject from sunburn or sun damage when the subject is exposed to, for example, sun light or other source of UVA and/or UVB radiation.

It is understood that the protection afforded by a topical composition depends on a number of factors, such as the concentration of the UV-absorbing agent(s) in the topical composition, the thickness at which the topical composition is applied to the skin, and the UV radiation intensity (e.g., current UV index) at the time of application and use. In some embodiments, the topical composition comprising the UV-absorbing agent(s) reduces or prevents sunburn or erythema/pigmentation of the skin caused by UVA and/or UVB radiation.

A topical composition can be formulated to reduce or prevent sunburn or erythema/pigmentation of the skin caused by UVA and/or UVB radiation when the composition is formulation to contain at least 0.05 wt %, 0.5 wt %, 0.1 wt %, 10 wt %, 20 wt %, 40 wt % or 50 wt %. In another embodiment, the topical composition comprises 0.05 wt % to 50 wt %, 10 wt % to 40 wt %, 25 wt % to 50 wt % or 20 wt % to 40 wt % of the UVR-absorbing compound or pharmaceutically acceptable salt thereof.

XII. Methods of Use

Topical application of the compositions of the present disclosure to the hair or skin of a subject will provide enhanced protection against deleterious effects of ultraviolet radiation (UVR). Thus, the subject invention further provides a method for protecting skin and/or hair against the deleterious effects of solar radiation, more particularly UVR, which method comprises topically applying thereto an effective amount of the sunscreen compositions as described herein. An esthetically beneficial result of exposure of skin to UVR (i.e., light radiation wavelengths of from 280 nm to 400 nm) is the promotion of tanning of the epidermis. Another benefit of sun exposure comes from production of vitamin D within the skin. UVR is typically divided into UV-A (light wavelengths from 320 to 400 nm) and UV-B (wavelengths ranging from 280 to 320 nm) regions. Overexposure to UV-B irradiation is generally understood to lead to skin burns and erythema. In addition, overexposure to UV-A radiation may cause a loss of elasticity of the skin and the appearance of wrinkles, promoting premature skin aging. Such irradiation promotes triggering of the erythemal reaction or amplifies this reaction in certain individuals and may even be the source of phototoxic or photoallergic reactions. It is increasingly believed that overexposure to UV-A may also lead to melanoma. Thus, the application of the compositions of the invention to the skin and/or hair of an individual will provide enhanced UVR photoprotection (UV-A and/or UV-B) of the skin and/or hair of the individual.

The compositions of the disclosure are intended to provide a sun protection factor (SPF) rating of at least 2, with additional preferable embodiments having a sun protection factor of at least 5, at least 10, at least 15, at least 20, at least 25, at least 30, at least 35, at least 40, at least 45, at least 50, and at least 55.

XI. Examples

The following examples are illustrative in nature and are in no way intended to be limiting.

Example 1

Synthesis of Cyclohexen-1-[2-hydroxy-1-(hydroxymethyl)ethyl]amino]-2-Methoxy-3-N-[3-[(carboxymethyl)amino]-ylidenevia Cyclohexane The compounds of formula (I) may be prepared according to the routes described below and in the article by White et al., *J. Org. Chem.* 1995, 60:3600-3611 and the article by White et al., J. Am. Chem. Soc., 1989, 111:8970-8972.

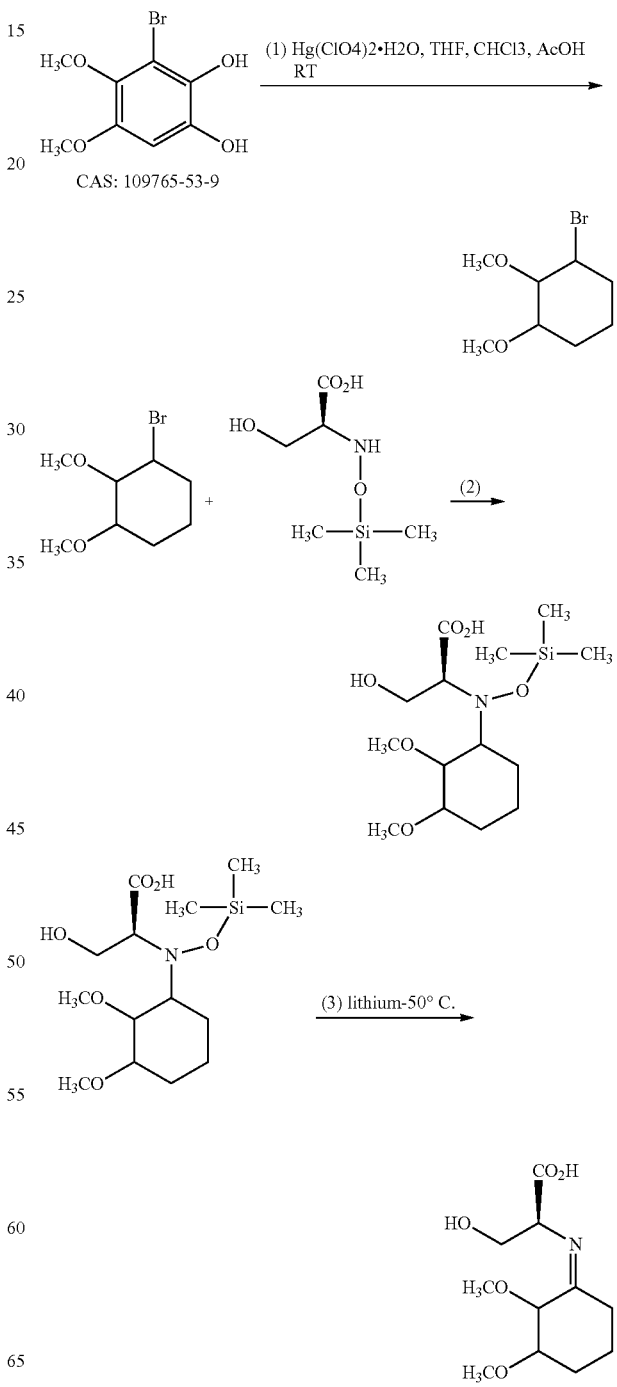

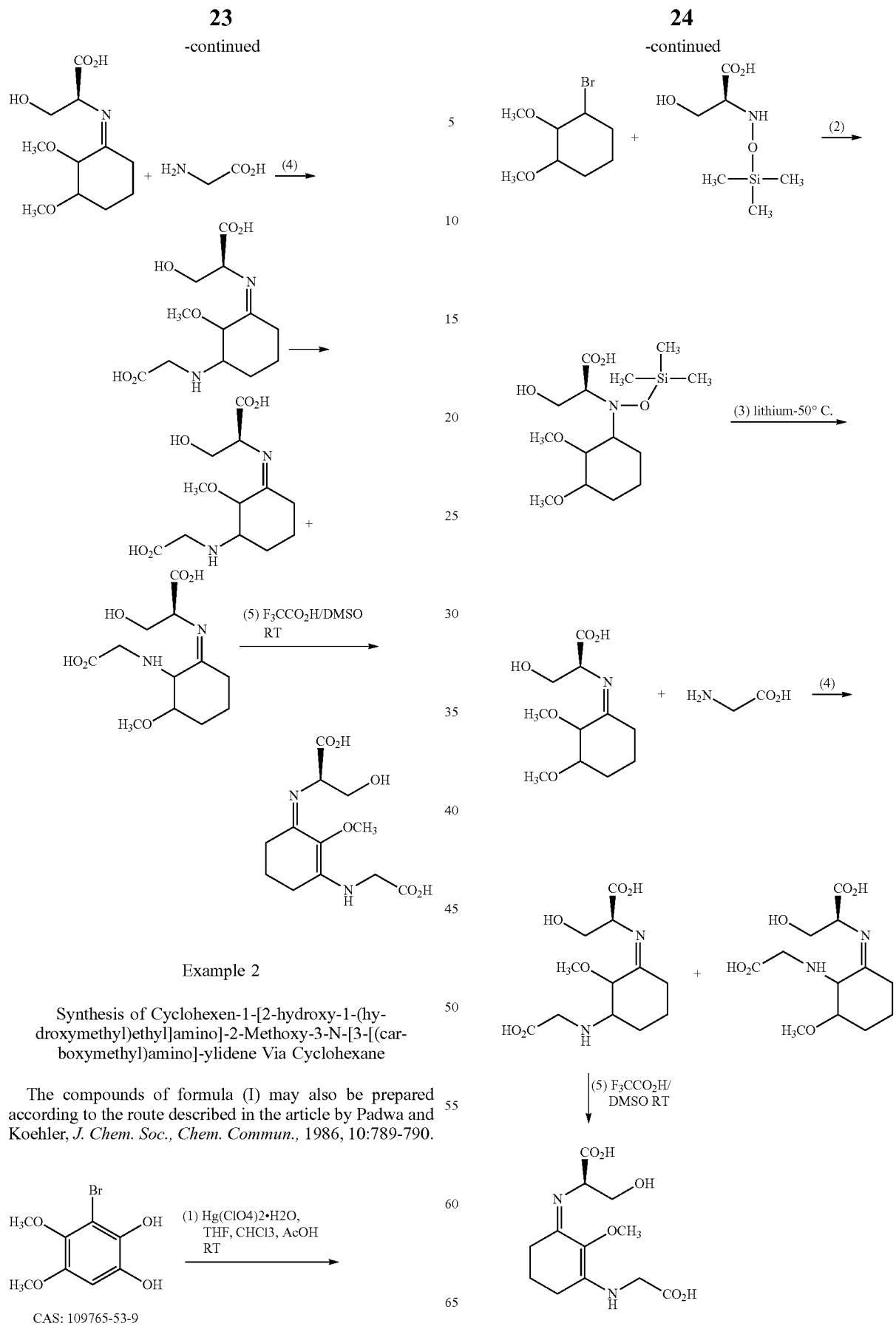
Example 2
Synthesis of Cyclohexen-1-[2-hydroxy-1-(hydroxymethyl)ethyl]amino]-2-Methoxy-3-N-[3-[(carboxymethyl)amino]-ylidene Via Cyclohexane
The compounds of formula (I) may also be prepared according to the route described in the article by Padwa and Koehler, *J. Chem. Soc., Chem. Commun.*, 1986, 10:789-790.

Example 3
Synthesis of 3-Hydroxy-2-methoxy-cyclo-2-enone (TopCHEM1), 2-methoxy-cyclohex-2-enone-3-amino acetic acid-TopCHEM-2), 2-methoxy-3-(imino glycine) cyclohex-1-ene-amino acetic acid (TopCHEM3)
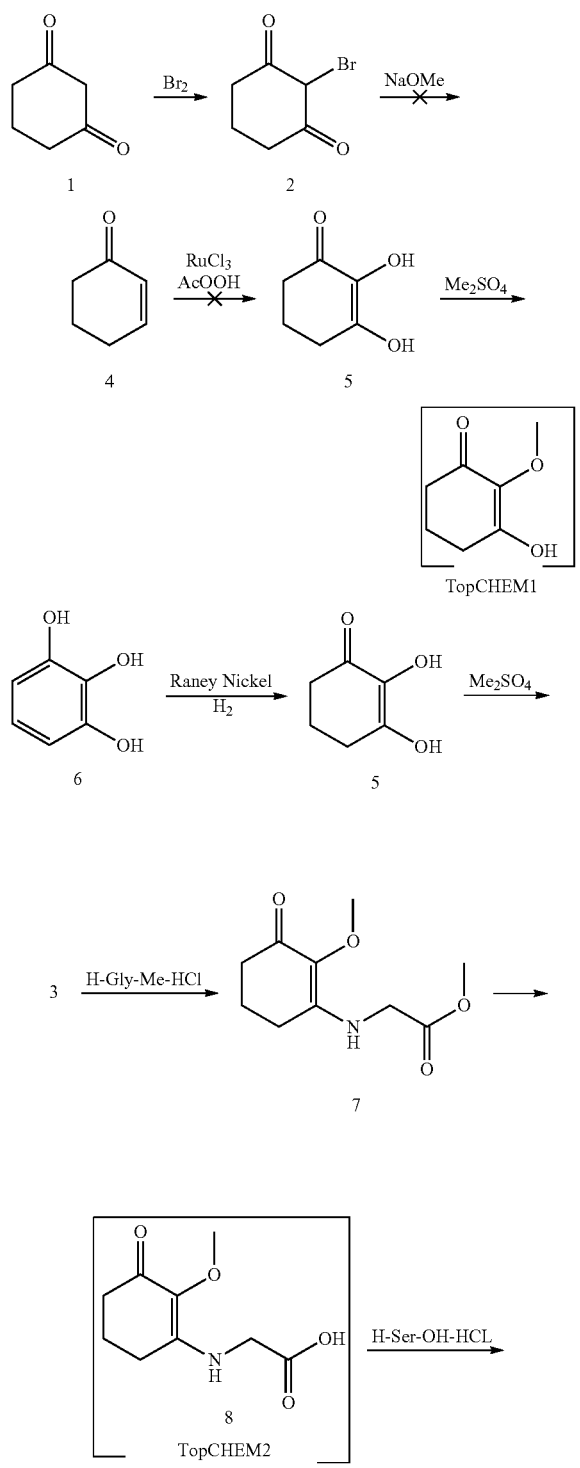
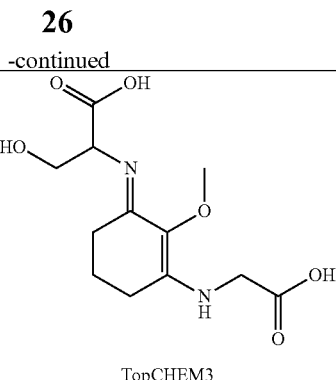
TopCHEM3
Example 4
Synthesis of 2-Methoxy-3-{(4-methoxyphenyl)imino} cyclohex-1-ene amino acetic acid (TopCHEM4)
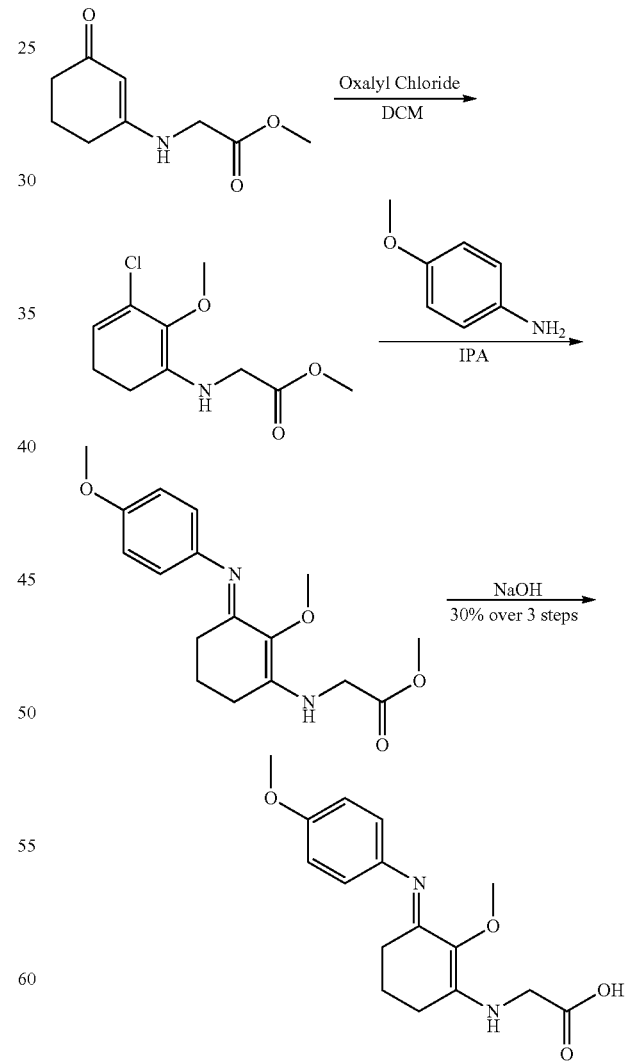
Purified by Reverse Phase Chromatography
Light brown powder

What is claimed is:

1. A compound of formula (II):

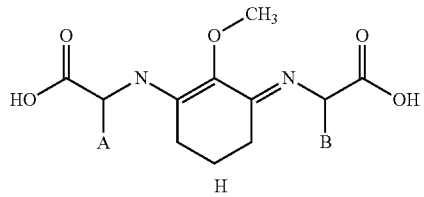

wherein
- A is H, CH$_3$ or CH(R)COOH, wherein R is H or an alkyl group with 1, 2 or 3 carbons; and
- B is H, CH$_3$ or CH(R)COOH, wherein R is H or an alkyl group with 1, 2 or 3 carbons.

2. The compound of claim 1, wherein A and B are the same.

3. A topical composition, comprising a compound of claim 1, a chemical sunscreen, a physical sunscreen, a pharmaceutically acceptable carrier, or a combination thereof.

4. The topical composition of claim 3, wherein the physical sunscreen comprises either zinc oxide or titanium oxide.

5. The topical composition of claim 3, further comprising an additional UV filter, wherein the additional UV filter comprises one or more of:
p-aminobenzoic acid, its salts and its derivatives; anthranilates; salicylates; cinnamic acid derivatives; dihydroxycinnamic acid derivatives; camphor derivatives; trihydroxycinnamic acid derivatives; hydrocarbons; dibenzalacetone; benzalacetophenone; naphtholsulfonates; dihydroxy-naphthoic acid and its salts; o- and p-hydroxydiphenyldisulfonates; coumarin derivatives; diazoles; quinine salts; quinoline derivatives; hydroxy- or methoxy-substituted benzophenones; uric acid derivatives; vilouric acid derivatives; tannic acid and its derivatives; hydroquinone; and benzophenones.

6. The topical composition of claim 3 wherein the compound is present in an oil-in-water or a water-in-oil emulsion.

7. The topical composition of claim 3, wherein at the time of initial application the composition has a sun protection factor (SPF) of at least 2, 15, 30, 50 or 60.

8. The topical composition of claim 3, further comprising a second compound which absorbs UVA and/or UVB radiation and is capable of providing protection against sunburn and skin-ageing, skin damage, and DNA damage.

9. The topical composition of claim 3, further comprising a second compound which absorbs UVA and/or UVB radiation, wherein the compound of claim 1 and the second compound have different UV absorbance characteristics.

10. A compound of formula (III):

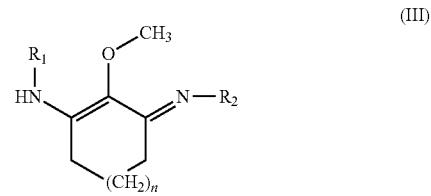

where n is selected from 1, 2, 3, and 4,
- R$_1$ and R$_2$ are each independently —(CH$_2$)$_m$—COOH or —(CH$_2$)$_y$—CH(A)-COOH, where
- m is an integer ranging from 1-9,
- y is an integer ranging from 0 to 8,
- A is a C1-C3 linear or branched alkyl or alkenyl optionally substituted at one or more carbon atoms, and
- wherein when C taken together with A forms a double bond, the H in CH(A) is absent such that the formula is —(CH$_2$)$_y$—C=(A)-COOH.

11. The compound of claim 10, wherein R$_1$ and R$_2$ are the same.

12. A topical composition, comprising a compound of claim 10, a chemical sunscreen, a physical sunscreen, a pharmaceutically acceptable carrier, or a combination thereof.

13. The topical composition of claim 12, wherein the compound is present in the composition at a concentration of about 0.05 wt % to 60 wt %.

* * * * *